(12) United States Patent
Baril et al.

(10) Patent No.: US 11,517,297 B2
(45) Date of Patent: *Dec. 6, 2022

(54) ROLLABLE TISSUE SPECIMEN BAG WITH IMPROVED BRIM FOR TENTING

(71) Applicant: Covidien LP, Mansfield, MA (US)

(72) Inventors: Jacob C. Baril, Norwalk, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 363 days.

This patent is subject to a terminal disclaimer.

(21) Appl. No.: 16/894,546

(22) Filed: Jun. 5, 2020

(65) Prior Publication Data

US 2021/0378647 A1 Dec. 9, 2021

(51) Int. Cl.
*A61B 17/00* (2006.01)

(52) U.S. Cl.
CPC ............ *A61B 17/00234* (2013.01); *A61B 2017/00287* (2013.01); *A61B 2017/00858* (2013.01); *A61B 2017/00867* (2013.01)

(58) Field of Classification Search
CPC .... A61B 17/00234; A61B 2017/00287; A61B 2017/00858; A61B 2017/00867; A61B 2017/00862

See application file for complete search history.

(56) References Cited

U.S. PATENT DOCUMENTS

| 5,480,404 | A | * | 1/1996 | Kammerer ....... A61B 17/00234 606/127 |
| 6,059,793 | A | | 5/2000 | Pagedas |
| 6,156,055 | A | | 12/2000 | Ravenscroft |
| 6,162,209 | A | | 12/2000 | Gobron et al. |
| 6,171,317 | B1 | | 1/2001 | Jackson et al. |
| 6,206,889 | B1 | | 3/2001 | Bennardo |
| 6,224,612 | B1 | | 5/2001 | Bates et al. |
| 6,228,095 | B1 | | 5/2001 | Dennis |
| 6,248,113 | B1 | | 6/2001 | Fina |
| 6,258,102 | B1 | | 7/2001 | Pagedas |
| 6,264,663 | B1 | | 7/2001 | Cano |
| 6,270,505 | B1 | | 8/2001 | Yoshida et al. |
| 6,280,451 | B1 | | 8/2001 | Bates et al. |
| 6,344,026 | B1 | | 2/2002 | Burbank et al. |
| 6,350,266 | B1 | | 2/2002 | White et al. |
| 6,350,267 | B1 | | 2/2002 | Stefanchik |

(Continued)

*Primary Examiner* — George J Ulsh
*Assistant Examiner* — Rachel S Highland
(74) *Attorney, Agent, or Firm* — Carter, DeLuca & Farrell LLP

(57) ABSTRACT

A tissue specimen retrieval bag assembly includes a tissue specimen bag having an open proximal end and a closed distal end, the proximal end including a cuff defined therein and extending therearound. A flexible bag brim is disposed within the cuff, the flexible bag brim transitionable between a first, collapsed configuration and a second, expanded configuration. The flexible bag brim includes a D-Shaped cross section configured to facilitate both furling the tissue specimen bag onto itself around the bag brim when the bag brim is disposed in the second, expanded configuration and securing the tissue specimen bag in a desired furled configuration. The flexible bag brim defines a cavity therein configured to facilitate compression thereof and to facilitate handling of the bag brim by a surgical instrument.

6 Claims, 11 Drawing Sheets

(56) References Cited

U.S. PATENT DOCUMENTS

| | | | |
|---|---|---|---|
| 6,358,198 | B1 | 3/2002 | Levin et al. |
| 6,368,328 | B1 | 4/2002 | Chu et al. |
| 6,383,195 | B1 | 5/2002 | Richard |
| 6,383,197 | B1 | 5/2002 | Conlon et al. |
| 6,387,102 | B2 | 5/2002 | Pagedas |
| 6,406,440 | B1 | 6/2002 | Stefanchik |
| 6,409,733 | B1 | 6/2002 | Conlon et al. |
| 6,447,523 | B1 | 9/2002 | Middleman et al. |
| 6,530,923 | B1 | 3/2003 | Dubrul et al. |
| 6,537,273 | B1 | 3/2003 | Sosiak et al. |
| 6,752,822 | B2 | 6/2004 | Jespersen |
| 6,805,699 | B2 | 10/2004 | Shimm |
| 6,951,533 | B2 | 10/2005 | Foley |
| 6,986,774 | B2 | 1/2006 | Middleman et al. |
| 7,037,275 | B1 | 5/2006 | Marshall et al. |
| 7,052,501 | B2 | 5/2006 | McGuckin, Jr. |
| 7,087,062 | B2 | 8/2006 | Dhindsa |
| 7,101,379 | B2 | 9/2006 | Gregory, Jr. et al. |
| 7,101,380 | B2 | 9/2006 | Khachin et al. |
| 7,112,172 | B2 | 9/2006 | Orban, III et al. |
| 7,115,125 | B2 | 10/2006 | Nakao et al. |
| 7,144,400 | B2 | 12/2006 | Byrum et al. |
| 7,169,154 | B1 | 1/2007 | Que et al. |
| 7,229,418 | B2 | 6/2007 | Burbank et al. |
| 7,285,126 | B2 | 10/2007 | Sepetka et al. |
| 7,316,692 | B2 | 1/2008 | Huffmaster |
| 7,357,801 | B2 | 4/2008 | Burbank et al. |
| 7,534,252 | B2 | 5/2009 | Sepetka et al. |
| 7,547,310 | B2 | 6/2009 | Whitfield |
| 7,615,013 | B2 | 11/2009 | Clifford et al. |
| 7,618,437 | B2 | 11/2009 | Nakao |
| 7,650,887 | B2 * | 1/2010 | Nguyen ............. A61B 17/3423 128/889 |
| 7,654,283 | B2 | 2/2010 | Seto et al. |
| 7,670,346 | B2 | 3/2010 | Whitfield |
| 7,678,118 | B2 | 3/2010 | Bates et al. |
| 7,722,626 | B2 | 5/2010 | Middleman et al. |
| 7,727,227 | B2 | 6/2010 | Teague et al. |
| 7,731,722 | B2 | 6/2010 | Lavelle et al. |
| 7,731,723 | B2 | 6/2010 | Kear et al. |
| 7,762,959 | B2 | 7/2010 | Bilsbury |
| 7,762,960 | B2 | 7/2010 | Timberlake et al. |
| 7,875,038 | B2 | 1/2011 | Que et al. |
| 7,892,242 | B2 | 2/2011 | Goldstein |
| 7,914,540 | B2 | 3/2011 | Schwartz et al. |
| 7,918,860 | B2 | 4/2011 | Leslie et al. |
| 7,955,292 | B2 | 6/2011 | Leroy et al. |
| 8,057,485 | B2 | 11/2011 | Hollis et al. |
| 8,075,567 | B2 | 12/2011 | Taylor et al. |
| 8,118,816 | B2 | 2/2012 | Teague |
| 8,152,820 | B2 | 4/2012 | Mohamed et al. |
| 8,172,772 | B2 | 5/2012 | Zwolinski et al. |
| 8,211,115 | B2 | 7/2012 | Cheng et al. |
| 8,282,572 | B2 | 10/2012 | Bilsbury |
| 8,337,510 | B2 | 12/2012 | Rieber et al. |
| 8,348,827 | B2 | 1/2013 | Zwolinski |
| 8,409,216 | B2 | 4/2013 | Parihar et al. |
| 8,414,596 | B2 | 4/2013 | Parihar et al. |
| 8,419,749 | B2 | 4/2013 | Shelton, IV et al. |
| 8,425,533 | B2 | 4/2013 | Parihar et al. |
| 8,430,826 | B2 | 4/2013 | Uznanski et al. |
| 8,435,237 | B2 | 5/2013 | Bahney |
| 8,444,655 | B2 | 5/2013 | Parihar et al. |
| 8,486,087 | B2 | 7/2013 | Fleming |
| 8,512,351 | B2 | 8/2013 | Teague |
| 8,579,914 | B2 | 11/2013 | Menn et al. |
| 8,585,712 | B2 | 11/2013 | O'Prey et al. |
| 8,591,521 | B2 | 11/2013 | Cherry et al. |
| 8,652,147 | B2 | 2/2014 | Hart |
| 8,721,658 | B2 | 5/2014 | Kahle et al. |
| 8,734,464 | B2 | 5/2014 | Grover et al. |
| 8,777,961 | B2 | 7/2014 | Cabrera et al. |
| 8,795,291 | B2 | 8/2014 | Davis et al. |
| 8,821,377 | B2 | 9/2014 | Collins |
| 8,827,968 | B2 | 9/2014 | Taylor et al. |
| 8,870,894 | B2 | 10/2014 | Taylor et al. |
| 8,906,035 | B2 | 12/2014 | Zwolinski et al. |
| 8,956,370 | B2 | 2/2015 | Taylor et al. |
| 8,968,329 | B2 | 3/2015 | Cabrera |
| 8,986,321 | B2 | 3/2015 | Parihar et al. |
| 9,005,215 | B2 | 4/2015 | Grover et al. |
| 9,017,328 | B2 | 4/2015 | Bahney |
| 9,017,340 | B2 | 4/2015 | Davis |
| 9,033,995 | B2 | 5/2015 | Taylor et al. |
| 9,084,588 | B2 | 7/2015 | Farascioni |
| 9,101,342 | B2 | 8/2015 | Saleh |
| 9,113,848 | B2 | 8/2015 | Fleming et al. |
| 9,113,849 | B2 | 8/2015 | Davis |
| 9,308,008 | B2 | 4/2016 | Duncan et al. |
| 9,364,201 | B2 | 6/2016 | Orban, III |
| 9,364,202 | B2 | 6/2016 | Menn et al. |
| 9,370,341 | B2 | 6/2016 | Ceniccola et al. |
| 9,370,378 | B2 | 6/2016 | O'Prey et al. |
| 9,375,224 | B2 | 6/2016 | Jansen |
| 9,414,817 | B2 | 8/2016 | Taylor et al. |
| 9,468,542 | B2 | 10/2016 | Hurley et al. |
| 9,486,188 | B2 | 11/2016 | Secrest et al. |
| 9,522,034 | B2 | 12/2016 | Johnson et al. |
| 9,549,747 | B2 | 1/2017 | Carlson |
| 9,579,115 | B2 | 2/2017 | Kahle et al. |
| 9,592,067 | B2 | 3/2017 | Hartoumbekis |
| 9,622,730 | B2 | 4/2017 | Farascioni |
| 9,624,638 | B2 | 4/2017 | Lebreton et al. |
| 9,629,618 | B2 | 4/2017 | Davis et al. |
| 9,655,644 | B2 | 5/2017 | Collins |
| 9,730,716 | B2 | 8/2017 | Secrest et al. |
| 9,789,268 | B2 | 10/2017 | Hart et al. |
| 9,808,228 | B2 | 11/2017 | Kondrup et al. |
| 9,826,997 | B2 | 11/2017 | Cherry et al. |
| 9,867,600 | B2 | 1/2018 | Parihar et al. |
| 9,877,893 | B2 | 1/2018 | Taylor et al. |
| 10,932,767 | B2 * | 3/2021 | Naga Kalepu ..... A61B 17/0218 |

\* cited by examiner

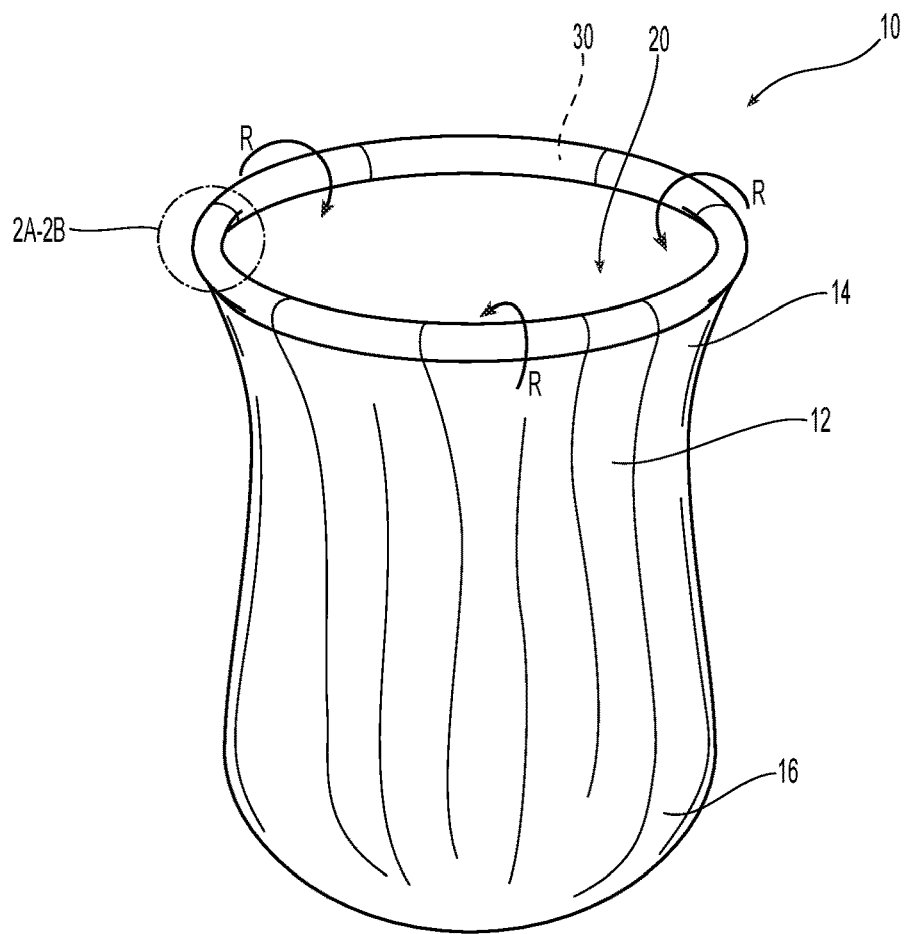
Fig. 1
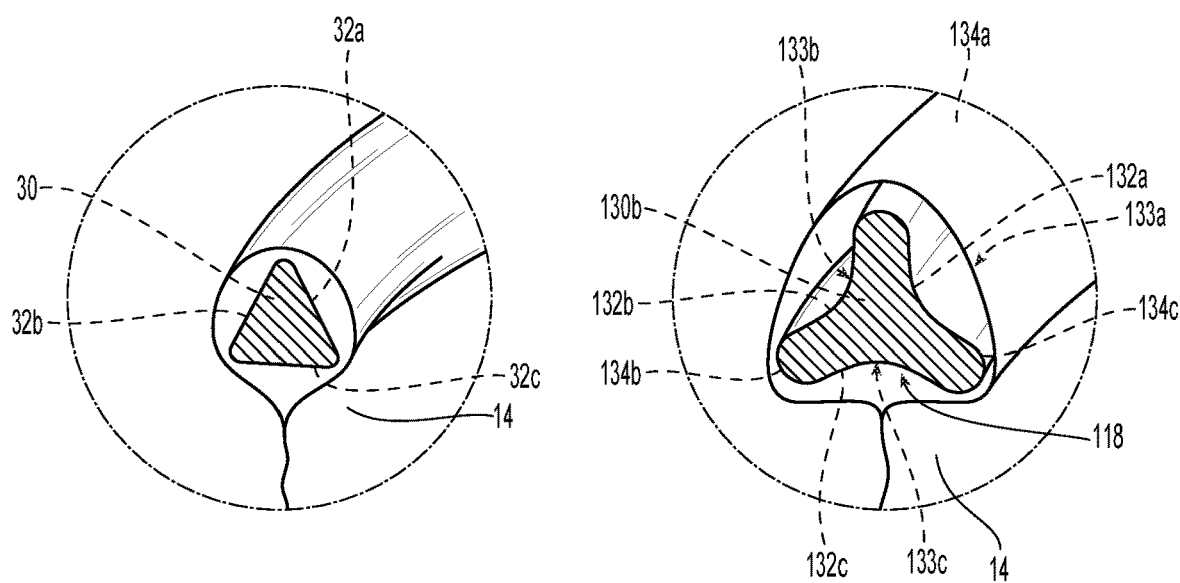
Fig. 2A
Fig. 2B

ROLLABLE TISSUE SPECIMEN BAG WITH IMPROVED BRIM FOR TENTING

BACKGROUND

Technical Field

The present disclosure relates to tissue specimen retrieval from an internal body cavity and, more particularly, to specimen retrieval or specimen containment bags that facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment such as a specimen retrieval bag or containment bag is highly desirable to inhibit seeding of cancer cells. Thus, with respect to breaking down large tissue specimens for retrieval through minimally-invasive openings, there is the added challenge of doing so within an enclosed environment.

In these instances, a standalone tissue bag may be utilized to contain large tissue specimens such as a uterus for hysterectomies or fibroids for myomectomies. The specimen retrieval bag or containment bag typically includes a bag brim having a flexible wire support that is transitionable between a first collapsed configuration for insertion through an incision or natural body orifice and a second expanded configuration for encapsulating tissue specimens. The bag brim, once externalized, may be manipulated or rolled to enhance surgical access to the tissue specimen or "tent" the specimen as needed.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

In accordance with aspects of the present disclosure is a tissue specimen retrieval bag assembly that includes a tissue specimen bag having an open proximal end and a closed distal end, the proximal end including a cuff defined therein and extending therearound. A flexible bag brim is disposed within the cuff and is transitionable between a first, collapsed configuration and a second, expanded configuration, the flexible bag brim including a cross section configured to facilitate both furling the tissue specimen bag onto itself around the bag brim when the bag brim is disposed in the second, expanded configuration and securing the tissue specimen bag in a desired furled configuration. The flexible bag brim includes a plurality of scallops defined along an inner peripheral surface thereof configured to facilitate furling the tissue specimen bag onto itself.

In aspects according to the present disclosure, at least one of the plurality of scallops includes at least one of a vent or a gate configured to facilitate manufacturing the flexible bag brim. In other aspects according to the present disclosure, the flexible bag brim includes a concave surface defined along an outer peripheral surface thereof. In still other aspects according to the present disclosure, the cross section includes a D-shaped cross section or a tri-lobular cross section. In yet other aspects according to the present disclosure, the cross section is tri-lobular and includes two or more edges that define a concave section therebetween configured to facilitate gripping the tissue specimen bag when furling.

In aspects according to the present disclosure, the tissue specimen bag is made from nylon and/or polyurethane.

In accordance with aspects of the present disclosure is a tissue specimen retrieval bag assembly that includes a tissue specimen retrieval bag assembly that includes a tissue specimen bag having an open proximal end and a closed distal end, the proximal end including a cuff defined therein and extending therearound. A flexible bag brim is disposed within the cuff and is transitionable between a first, collapsed configuration and a second, expanded configuration, the flexible bag brim including a cross section configured to facilitate both furling the tissue specimen bag onto itself around the bag brim when the bag brim is disposed in the second, expanded configuration and securing the tissue specimen bag in a desired furled configuration. The flexible bag brim includes a plurality of slots defined therethrough configured to facilitate handling of the flexible bag brim with a surgical instrument.

In aspects according to the present disclosure, the flexible bag brim includes a concave surface defined along an outer peripheral surface thereof. In other aspects according to the present disclosure, the cross section includes a tri-lobular cross section.

In aspects according to the present disclosure, the cross section is tri-lobular and includes at least two edges that define a concave section therebetween configured to facilitate gripping the tissue specimen bag when furling. In other aspects according to the present disclosure, the plurality of slots allows handling of the flexible bag brim by a medical instrument in a direction parallel to the flexible bag brim.

In accordance with aspects of the present disclosure is a tissue specimen retrieval bag assembly that includes a tissue specimen retrieval bag assembly that includes a tissue specimen bag having an open proximal end and a closed distal end, the proximal end including a cuff defined therein and extending therearound. A flexible bag brim is disposed within the cuff and is transitionable between a first, collapsed configuration and a second, expanded configuration, the flexible bag brim including a cross section configured to facilitate both furling the tissue specimen bag onto itself around the bag brim when the bag brim is disposed in the second, expanded configuration and securing the tissue specimen bag in a desired furled configuration. The flexible bag brim includes a rim disposed along an inner periphery thereof, the rim including a plurality of slots defined therethrough configured to facilitate handling of the flexible bag brim with a surgical instrument.

In aspects according to the present disclosure, the flexible bag brim includes a concave surface defined along an outer peripheral surface thereof. In other aspects according to the present disclosure, the cross section includes a tri-lobular cross section.

In aspects according to the present disclosure, the plurality of slots in the rim allows handling of the flexible bag brim by a medical instrument in a direction perpendicular to the flexible bag brim. In yet other aspects according to the present disclosure, the flexible bag brim includes a plurality of second slots defined therethrough configured to facilitate handling of the flexible bag brim with a surgical instrument in a direction parallel to the flexible bag brim.

In accordance with other aspects of the present disclosure is a tissue specimen retrieval bag assembly that includes a tissue specimen retrieval bag assembly includes a tissue specimen bag having an open proximal end and a closed distal end, the proximal end including a cuff defined therein and extending therearound. A flexible bag brim is disposed within the cuff, the flexible bag brim transitionable between a first, collapsed configuration and a second, expanded configuration. The flexible bag brim includes a D-Shaped cross section configured to facilitate both furling the tissue specimen bag onto itself around the bag brim when the bag brim is disposed in the second, expanded configuration and securing the tissue specimen bag in a desired furled configuration. The flexible bag brim defines a cavity therein configured to facilitate compression thereof and to facilitate handling of the bag brim by a surgical instrument.

In aspects according to the present disclosure, the tissue specimen bag is made from nylon and/or polyurethane. In other aspects according to the present disclosure, an outer peripheral surface of the bag brim includes a high friction material to facilitate gripping the tissue specimen bag when furling. In yet other aspects according to the present disclosure, the cavity is filled with a compressible liquid gel.

In aspects according to the present disclosure, a thickness of the walls of the bag brim is in the range of about 0.035 inches to about 0.055 inches. In other aspects according to the present disclosure, the thickness of the walls of the bag brim is dependent on the material of the bag brim to strike a balance between compressibility of the bag brim and furling rigidity thereof.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

FIG. 1 is a perspective view of a tissue specimen bag provided in accordance with aspects of the present disclosure;

FIG. 2A is a cross sectional view of the area of detail of FIG. 1 showing one embodiment of a tri-lobular, rollable bag brim design;

FIG. 2B is a cross sectional view of the area of detail of FIG. 1 showing another embodiment of a tri-lobular, rollable bag brim design;

FIG. 3A is a perspective view of another embodiment of a tissue specimen retrieval bag having a flexible wire-like bag brim according to the present disclosure;

FIG. 3B is an enlarged view of the area of detail of FIG. 3A;

FIG. 10B is a perspective, cross sectional comparison view of the rollable bag brim of FIG. 10A compared to a prior art bag brim.

DETAILED DESCRIPTION

Figure 3C:
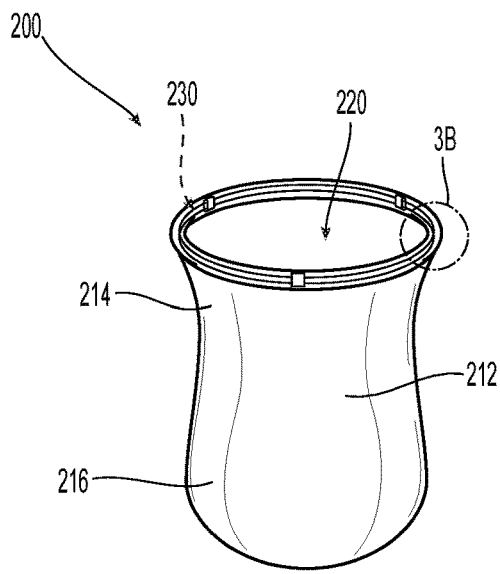
FIG. 3C is an enlarged view of the wire-like bag brim of FIG. 3A detached from the tissue specimen retrieval bag.
Figure 3C:
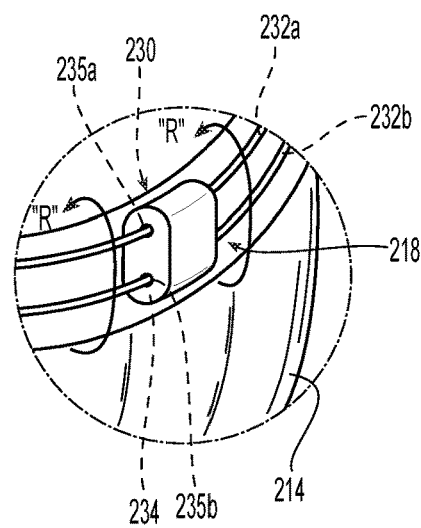
Figure 3C:
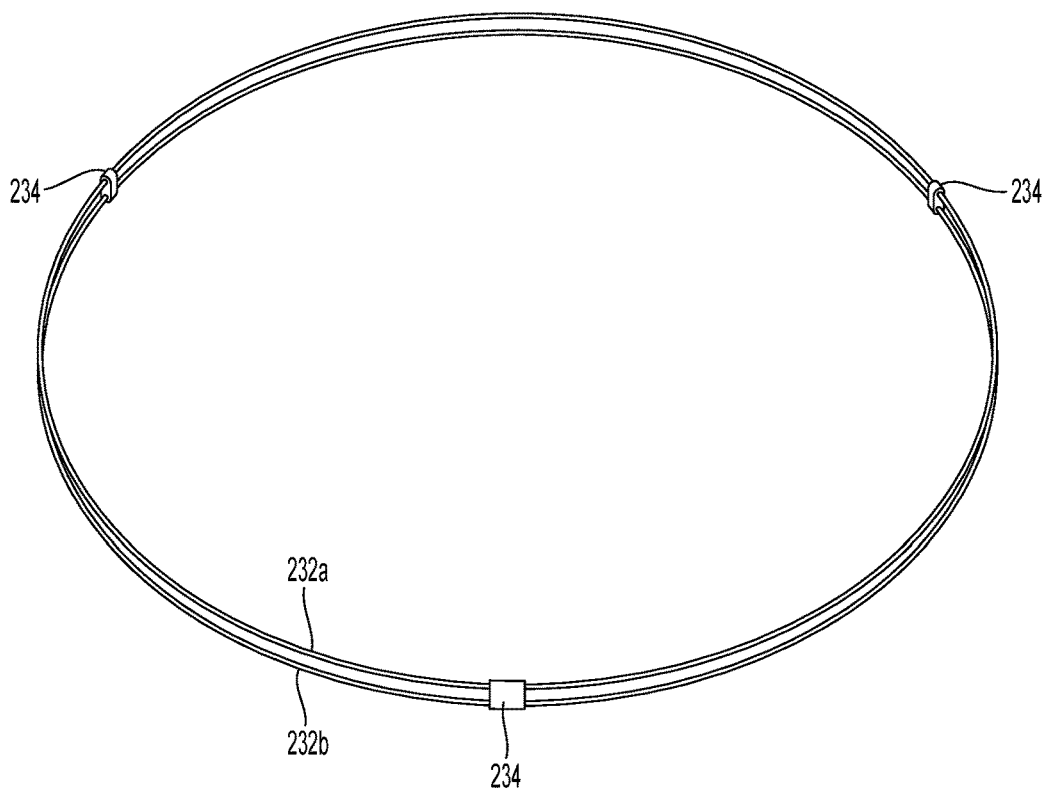

Turning initially to FIGS. 1-2A, one embodiment of a standalone tissue specimen retrieval bag or tissue containment bag assembly is shown and is represent by reference numeral 10. Bag assembly 10 includes a bag 12 having a proximal end 14 including an opening 20 defined therein and an enclosed distal end 16. Bag assembly 10 includes bag rim 30 that is configured to support bag 12 in such a fashion as to define opening 20 when the bag 12 is unfurled or in an open configuration. Opening 20 is of sufficient dimension to receive one or more tissue specimens "T" during a particular surgical procedure.

Bag rim 30 is configured to be flexible such that the bag brim 30 is easily transitionable between a first, collapsed configuration wherein the bag 12 is furled (as explained below) and a second, expanded configuration which allows the bag 12 to be unfurled for receipt of a tissue specimen "T". As such, bag brim 30 may be made from any flexible material that is easily expandable from a collapsed configuration. Bag 12 may include any suitable rollable material such as nylon, polyurethane, etc.

Turning now to FIG. 2A, the bag brim 30 is configured to seat within an elongated cuff 18 defined in the proximal end of the bag 12. More particularly, bag brim 30 is of sufficient dimension to fit within the cuff 18 along an entire length thereof. Bag brim 30 may include two mating ends that, when engaged, form a generally circular configuration when opened to support bag 12 thereon. Bag brim 30 is generally triangular in shape and includes three sides 32a, 32b and 32c. Other geometric configurations or multi-sided arrangements are also envisioned and may be tailored for a particular purpose.

The generally triangular shape of the bag brim 30 allows the bag 12 to roll or furl around itself which, in turn, allows a surgeon to tent (i.e., position) the tissue specimen "T" closer to the proximal end of the operating cavity as needed for dissection. More particularly, the geometry of the sides 32a, 32b and 32c of the bag brim 30 facilitate furling/unfurling the bag 12 as needed and securing the bag 12 in a desired furled position. Although generally illustrated in the various embodiments described herein as being rolled or furled inwardly, it is contemplated that the bag 12 may be rolled either inwardly or outwardly about the bag brim 30.

In use, the specimen "T" is placed into the specimen bag 12 through opening 20. The weight of the specimen "T" causes the specimen "T" to fall to toward the distal end 16 of the bag 12. The proximal end 14 of the bag 12 and the circularly-shaped bag brim 30 maintain the proximal end 14 the bag 12 outside the operating cavity (See for example, FIG. 5C). If the surgeon desires to bring the specimen "T" closer to the proximal end 14 of the bag 12, the surgeon furls the bag 12 around the bag brim 30 in the direction "R". The triangular shape of the bag brim 30 facilitates furling the bag 12 and the brim 30 over on itself which, in turn, allows the surgeon to position the tissue specimen "T" at a desired depth "L" (See for example, FIG. 5B) within the surgical cavity depending upon a particular purpose. The sides 32a, 32b and 32c of the bag brim 30 may include a high friction surface to facilitate gripping the bag 12 when furling.

FIG. 2B shows an alternative triangular-shaped bag brim 130 disposed within a cuff 118 having three generally rounded sides 132a, 132b and 132c separated by concave sections 133a, 133b and 133c, i.e., a tri-lobular-shaped cross section. The concave sections 133a, 133b and 133c allow the bag 12 to furl into a tighter configuration due to the geometry of the concave sections 133a, 133b and 133c. Moreover, each concave edge 134a, 134b and 134c of the bag brim 130 facilitates gripping the bag 12 during furling allowing a tighter and more secure furl. The concave edges 134a, 134b and 134c of the bag brim 130 may include a high friction surface to facilitate gripping the bag 12 when furling.

FIGS. 3A-3B show another embodiment of a tissue specimen retrieval bag assembly 200 for use with containing and supporting tissue specimens "T" within a surgical cavity. More particularly, bag assembly 200 includes a bag brim 230 having a bag 212 that depends therefrom for containing a tissue specimen "T". Bag brim 230 is disposed within a cuff 218 defined in a proximal end 214 of the bag 212. Bag brim 230 includes a pair of wires 232a, 232b that form the bag brim frame. A series of connectors or spacers 234 are spaced about the bag brim 230 and connect the two wires 232a, 232b together. More particularly, each connector 234 includes a pair of throughholes 235a, 235b defined therein that are each configured to receive a respective wire 232a, 232b of the bag brim 230. The number of connectors 234 depends on the type of wire 232a, 232b and the size of the bag brim 230. More connectors 234 will provide more consistent spacing along the bag brim 230.

In use and much like the embodiments shown in FIGS. 2A and 2B, a distal end 2116 of the bag 212 is placed within an operating cavity and a tissue specimen "T" is positioned through opening 220 of bag 212. The geometry of the bag brim 230 facilitates furling/unfurling the bag 212 as needed and secures the bag 212 in a desired furled position. More particularly, the shape of the bag brim 230 facilitates furling the bag 212 and the brim 230 in the direction of rotation "R" over on itself which, in turn, allows the surgeon to position the tissue specimen "T" at a desired depth "L" (See for example, FIG. 5B) within the surgical cavity depending upon a particular purpose.

The wires 232a, 232b may be made of any know wire that is flexible such that the bag brim 230 is easily transitionable between a first collapsed configuration wherein the bag 212 is furled and a second expanded configuration which allows the bag 212 to be unfurled for receipt of a tissue specimen "T", e.g., a shape memory alloy (SMA) such as nickel-titanium alloy commonly sold under the tradename Nitinol® or copper-aluminum-nickel. Bag 212 may include any suitable rollable material such as nylon, polyurethane, etc.

Figure 4A:
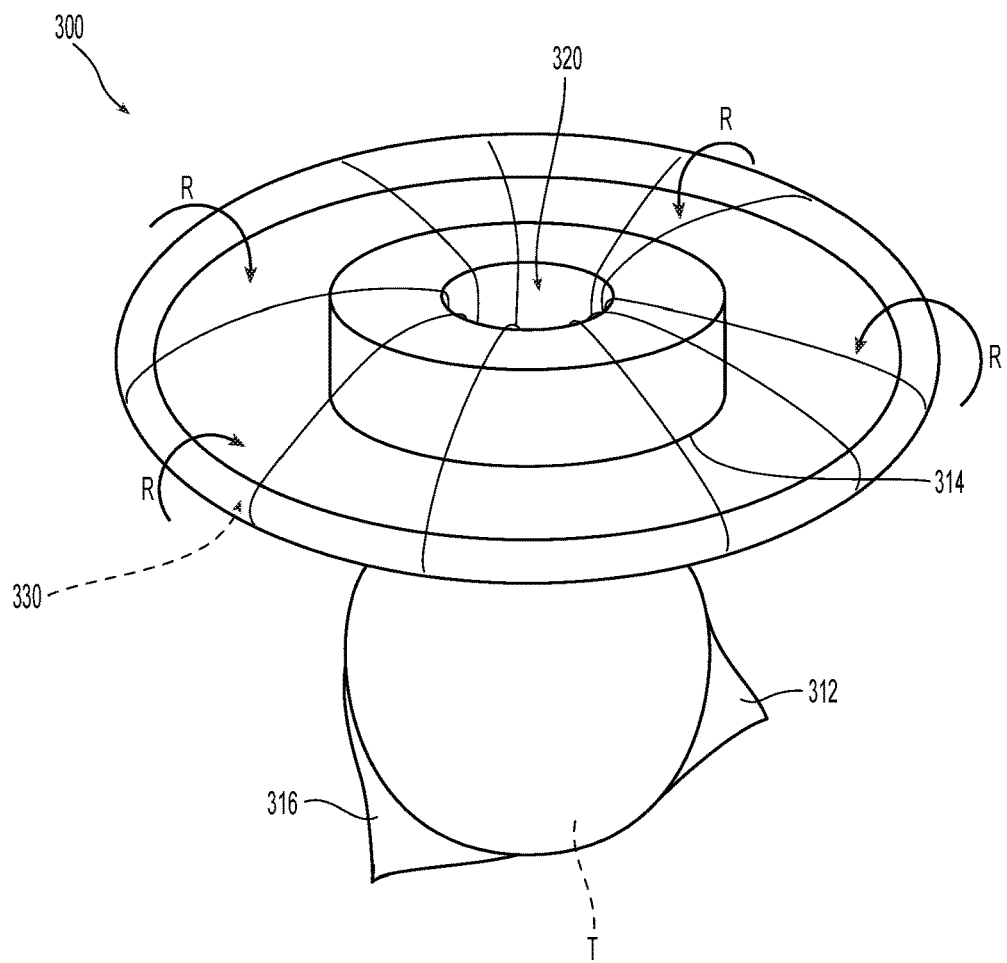
FIG. 4A is a perspective view of another embodiment of a tissue specimen retrieval bag having a rollable bag brim according to the present disclosure.
Figure 4B:
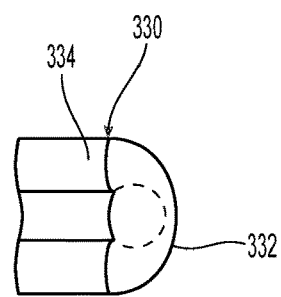
FIG. 4B is an enlarged, cross sectional view of the rollable bag brim of FIG. 4A.
Figure 5C:
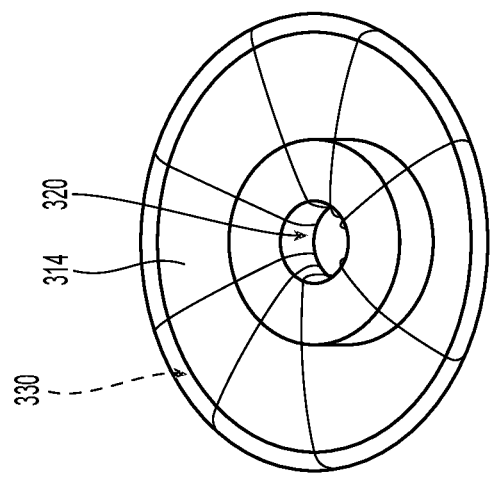
FIGS. 5A-5C are various views of the tissue specimen retrieval bag of FIGS. 4A and 4B for use with a tissue specimen "T"

FIGS. 4-5C show another embodiment of a tissue specimen retrieval bag assembly 300 for use with containing and supporting tissue specimens "T" within a surgical cavity. More particularly, bag assembly 300 includes a bag brim 330 having a bag 312 that depends therefrom for containing a tissue specimen "T". Bag brim 330 is disposed within a cuff (not shown) defined in a proximal end 314 of the bag 312. Bag brim 330 is generally D-shaped and includes an arcuate side 332 and a generally flat side 334. Much like the embodiments shown above, the generally D-shaped bag brim 330 allows the bag 312 to roll or furl around itself which, in turn, allows a surgeon to tent (i.e., position) the tissue specimen "T" closer to the proximal end of the operating cavity as needed for dissection.

Figure 5B:
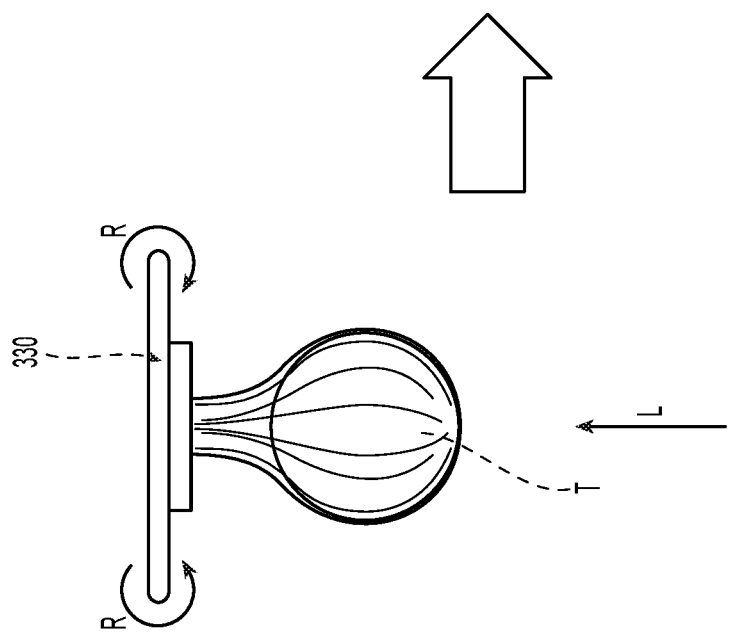
Figure 5A:
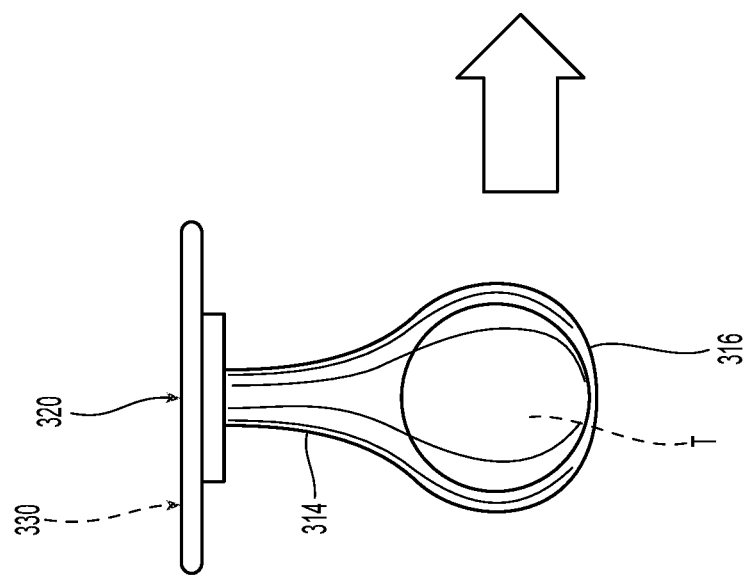

More particularly, and as best shown in FIGS. 5A-5C, the geometry of the sides 332, 334 of the bag brim 330 facilitate furling/unfurling the bag 312 as needed and securing the bag 312 in a desired furled position. As shown in FIG. 5A, the specimen "T" is place into the specimen bag 312 through opening 320. The weight of the specimen "T" causes the specimen "T" to fall to toward the distal end 316 of the bag 312. The proximal end 314 of the bag 312 and the circularly-shaped bag brim 330 maintain the proximal end 314 the bag 312 outside the operating cavity (See FIG. 5C). If the surgeon desires to bring the specimen "T" closer to the proximal end 314 of the bag 312, the surgeon furls the bag 312 around the bag brim 330 in the direction "R". The D-shape of the bag brim 330 facilitates furling the bag 312 and the brim 330 over on itself which, in turn, allows the surgeon to position the tissue specimen "T" at a desired depth "L" within the surgical cavity depending upon a particular purpose (See FIG. 5B). The flat side 334 and/or the arcuate side 332 may include a high friction surface to facilitate gripping the bag 312 when furling.

Figure 6A:
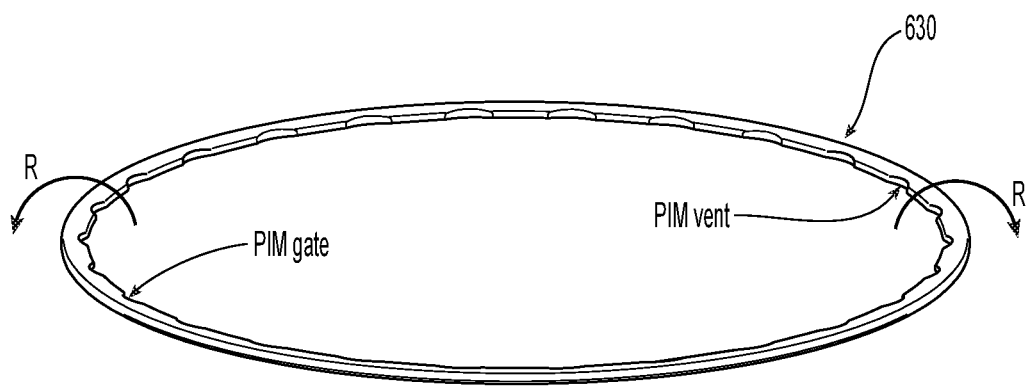
FIG. 6A is a perspective view of another embodiment of a rollable bag brim according another embodiment of the present disclosure.
Figure 6B:
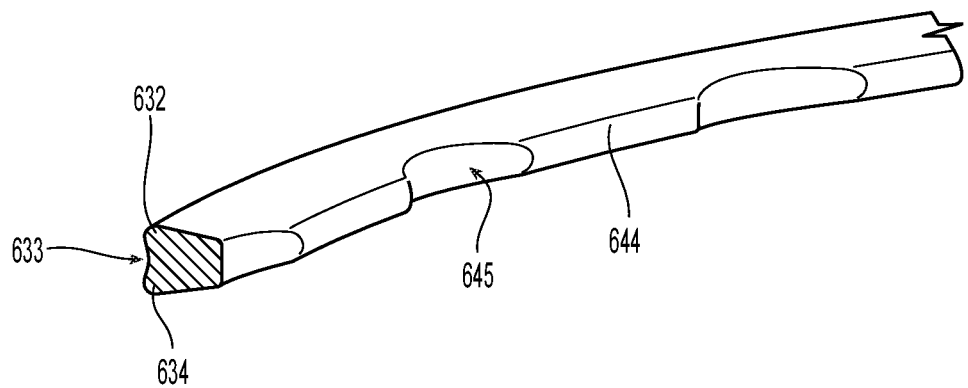
FIG. 6B is an enlarged, perspective view of the rollable bag brim of FIG. 6A.

FIGS. 6A and 6B show an alternate embodiment of a bag brim 630 for use with a tissue specimen retrieval bag 300.

Bag brim 630 is generally circular-shaped much like the above-described bag brims. Bag brim 630 is configured to be flexible such that the bag brim 630 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 630 may be made from any flexible material that is easily expandable from a collapsed configuration. Bag brim 630 may include a D-shaped cross section or may include a tri-lobular cross section (as explained in more detail below).

Bag brim 630 includes flexible upper and lower rims 632, 634, respectively, joined by a concave section 633 defined therebetween. Concave section 633 facilitates attachment of the bag 12 to the bag brim 630, e.g., via welding, gluing or melting thereon. A series of scallops 645 are defined along an inner peripheral surface 644 of the bag brim 630 and are configured to facilitate furling the bag 12 with minimal rotational force (e.g., force in the direction "R"). For example, the scallops 645 make furling the brim 630 easier due to the varying cross section of the bag brim 630 along the periphery 644 while at the same time maintaining the overall rigidity of the bag brim 630 for securing the bag 12 when tenting.

The scallops 645 may be "snapped off" or otherwise removed after molding. Moreover, as shown in FIG. 6A, the scallops 645 may allow good gating (PIM gate) and venting (PIM vent) locations during molding. More particularly, the rounded nature of the flexible brim 630 make it difficult to provide an area for gating and venting. The scallops 645 provide a larger flat area facilitating access for one or more injection molding gate or vent areas.

Figure 7A:
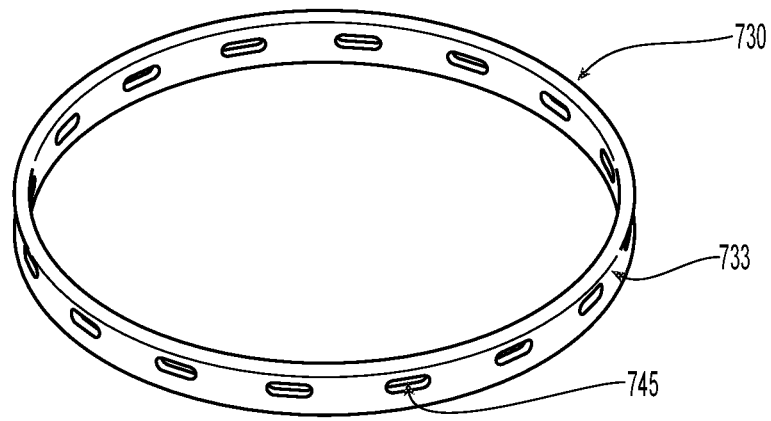
FIG. 7A is a perspective view of another embodiment of a rollable bag brim according another embodiment of the present disclosure.
Figure 7B:
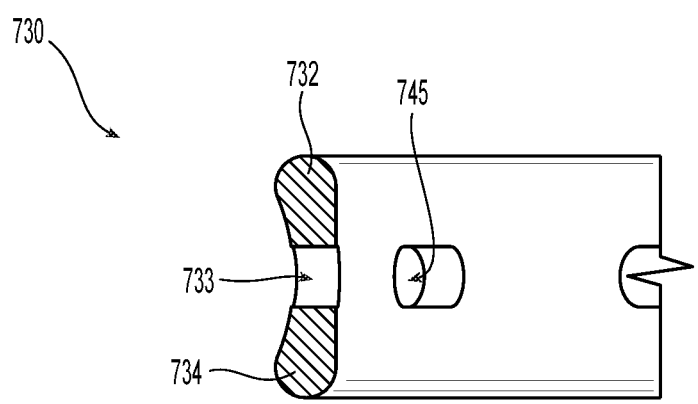
FIG. 7B is an enlarged, cross sectional view of the rollable bag brim of FIG. 7A.

FIGS. 7A and 7B show an alternate embodiment of a bag brim 730 for use with a tissue specimen retrieval bag 300. Bag brim 730 is generally circular-shaped and much like the above-described bag brims, bag brim 730 is configured to be flexible such that the bag brim 730 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 730 may be made from any flexible material that is easily expandable from a collapsed configuration.

Bag brim 730 includes flexible upper and lower rims 732, 734, respectively, joined by a concave section 733 defined therebetween. Concave section 733 facilitates attachment of the bag 12 to the bag brim 730, e.g., via welding, gluing or melting thereon. Moreover, concave section 733 facilitates furling the bag 12 with minimal rotational force for tenting purposes.

Figure 7C:
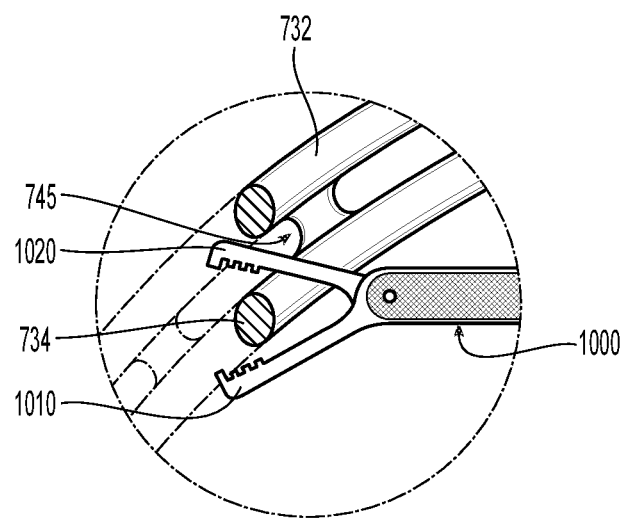
FIG. 7C is an enlarged, cross sectional view of the rollable bag brim of FIG. 7A illustrating manipulation thereof by a forceps.

A series of slots 745 are defined through the concave section 733 around the periphery of the bag brim 730 that facilitate grasping of the bag brim 730 therealong for manipulation purposes (see FIG. 7C.). More particularly, upper and lower jaw members 1010, 1020 of a forceps 1000 may easily grasp the bag bring 730 via engaging upper or lower rims 732, 734 of the bag brim 730 via slots 745. In this instance, a user is able to manipulate the bag brim 730 through the side thereof (in a coplanar or parallel direction).

Figure 8A:
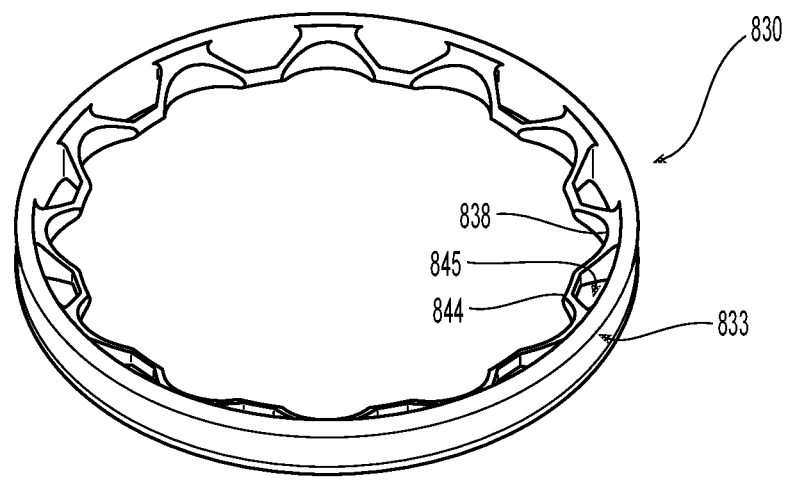
FIG. 8A is a perspective view of another embodiment of a rollable bag brim according another embodiment of the present disclosure.
Figure 8B:
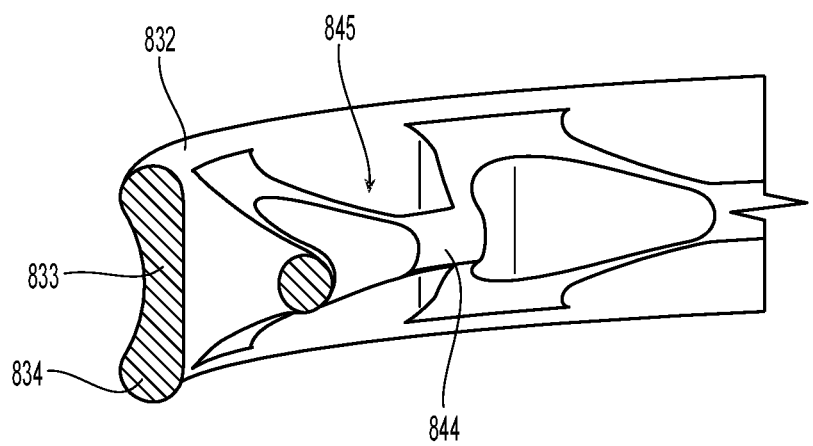
FIG. 8B is an enlarged, cross sectional view of the rollable bag brim of FIG. 8A.

FIGS. 8A and 8B show an alternate embodiment of a bag brim 830 for use with a tissue specimen retrieval bag 300. Bag brim 830 is generally circular-shaped and much like the above-described bag brims, bag brim 830 is configured to be flexible such that the bag brim 830 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 830 may be made from any flexible material that is easily expandable from a collapsed configuration.

Bag brim 830 includes flexible upper and lower rims 832, 834, respectively, joined by a concave section 833 defined therebetween. Concave section 833 facilitates attachment of the bag 12 to the bag brim 830, e.g., via welding, gluing or melting thereon. Moreover, concave section 833 facilitates furling the bag 12 with minimal rotational force for tenting purposes.

A rim 844 extends along the inner periphery 838 of bag brim 830 and defines a series of slots 845 therein configured to allow manipulation of the bag brim 830 by forceps 1000. More particularly, upper and lower jaw members 1010, 1020 of a forceps 1000 may easily grasp the bag brim 830 via engaging rim 844 through slots 845. In this instance, a user is able to manipulate the bag brim 830 from the top or bottom thereof (e.g., in a direction normal to the bag brim 830).

Figure 9A:
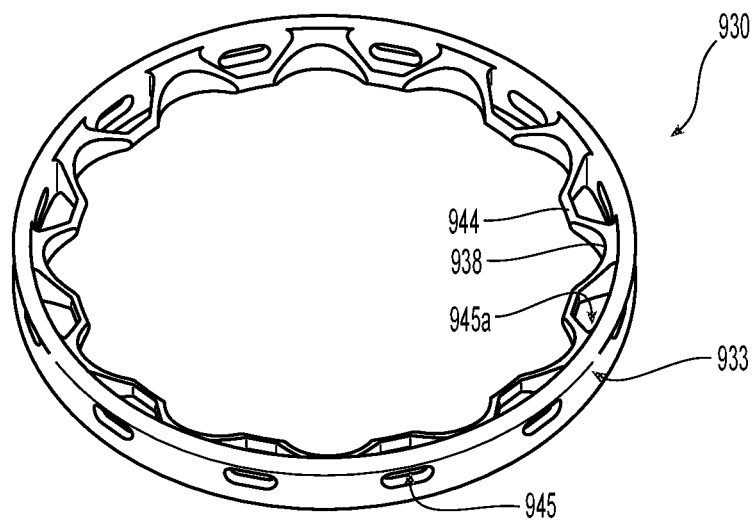
FIG. 9A is a perspective view of another embodiment of a rollable bag brim according another embodiment of the present disclosure.
Figure 9B:
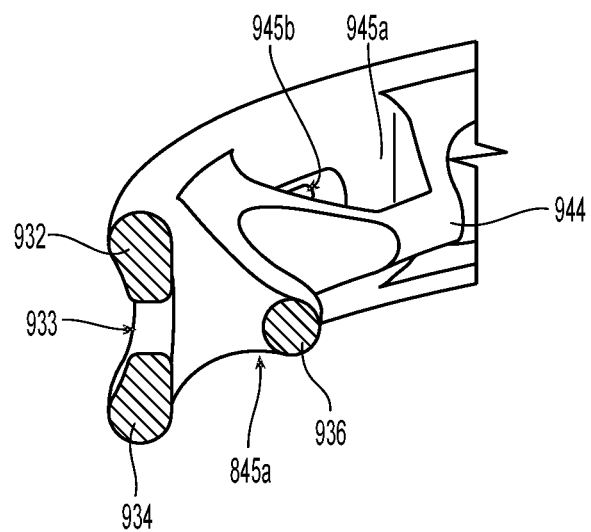
FIG. 9B is an enlarged, cross sectional view of the rollable bag brim of FIG. 9A.

FIGS. 9A and 9B show an alternate embodiment of a bag brim 930 for use with a tissue specimen retrieval bag 300. Bag brim 930 is essentially a combination of bag brim 730 and bag brim 830. More particularly, bag brim 930 is generally circular-shaped and much like the above-described bag brims, bag brim 930 is configured to be flexible such that the bag brim 930 is easily transitionable between a first, collapsed configuration wherein the bag, e.g., bag 12, is furled (as explained above) and a second, expanded configuration which allows the bag 12 to be unfurled for receipt of a tissue specimen "T". As such, bag brim 930 may be made from any flexible material that is easily expandable from a collapsed configuration.

Bag brim 930 includes flexible upper and lower rims 932, 934, respectively, joined by a concave section 933 defined therebetween. Concave section 933 facilitates attachment of the bag 12 to the bag brim 930, e.g., via welding, gluing or melting thereon. Moreover, concave section 933 facilitates furling the bag 12 with minimal rotational force for tenting purposes.

A rim 944 extends along the inner periphery 938 of bag brim 930 and defines a series of slots 945a therein configured to allow manipulation of the bag brim 930 by forceps 1000. More particularly, upper and lower jaw members 1010, 1020 of a forceps 1000 may easily grasp the bag brim 930 via engaging rim 944 through slots 945a. In this instance, a user is able to manipulate the bag brim 930 from the top or bottom thereof (e.g., in a direction normal to the bag brim 930).

A series of slots 945b are also defined through the concave section 933 around the periphery of the bag brim 930 and facilitate grasping of the bag brim 930 therealong for manipulation purposes. More particularly, upper and lower jaw members 1010, 1020 of forceps 1000 may easily grasp the bag bring 930 via engaging upper or lower rims 932, 934 of the bag brim 930 via slots 945b. In this instance, a user is able to also manipulate the bag brim 930 through the side thereof (in a coplanar or parallel direction).

Figure 9C:
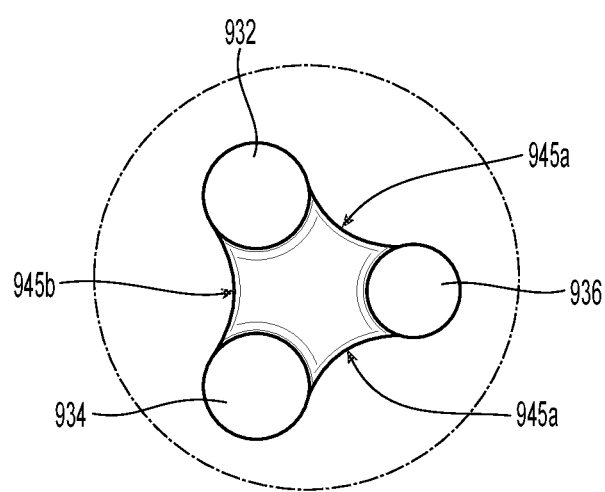
FIG. 9C is an enlarged, cross sectional view of the rollable bag brim of FIG. 9A illustrating a tri-lobular design for manipulation thereof by a forceps.

FIG. 9C shows a cross section of the bag brim 930 highlighting the tri-lobular profile. Essentially, the tri-lobular design of the bag brim 930 permits the forceps 1000 to grasp one of three sides 932, 934 and 936 of the bag brim through the top or side slots 945a, 945b.

FIGS. 10A-10C and 9B show an alternate embodiment of a bag brim 1030 for use with a tissue specimen retrieval bag 300. Bag brim 1030 is generally D-shaped and much like the above-described bag brims, bag brim 1030 is configured to be flexible such that the bag brim 1030 is easily transitionable between a first, collapsed configuration wherein the bag, e.g., bag 312, is furled (as explained above) and a second, expanded configuration which allows the bag 312 to be unfurled for receipt of a tissue specimen "T". As such, bag brim 1030 may be made from any flexible material that is easily expandable from a collapsed configuration.

Bag brim 1030 includes flexible upper and lower rims 1032, 1034, respectively, joined by a concave section 1033 defined therebetween. Concave section 1033 facilitates attachment of the bag 312 to the bag brim 1030, e.g., via welding, gluing or melting thereon. Moreover, concave section 1033 facilitates furling the bag 312 with minimal rotational force for tenting purposes.

Figure 10A:
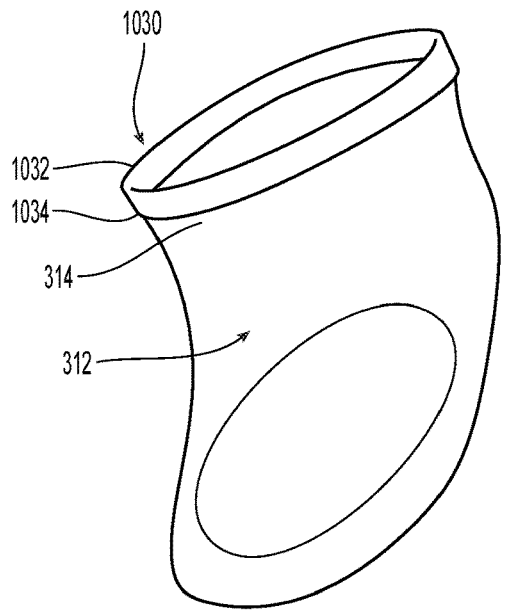
FIG. 10A is a perspective view of another embodiment of a rollable bag brim according another embodiment of the present disclosure.
Figure 10C:
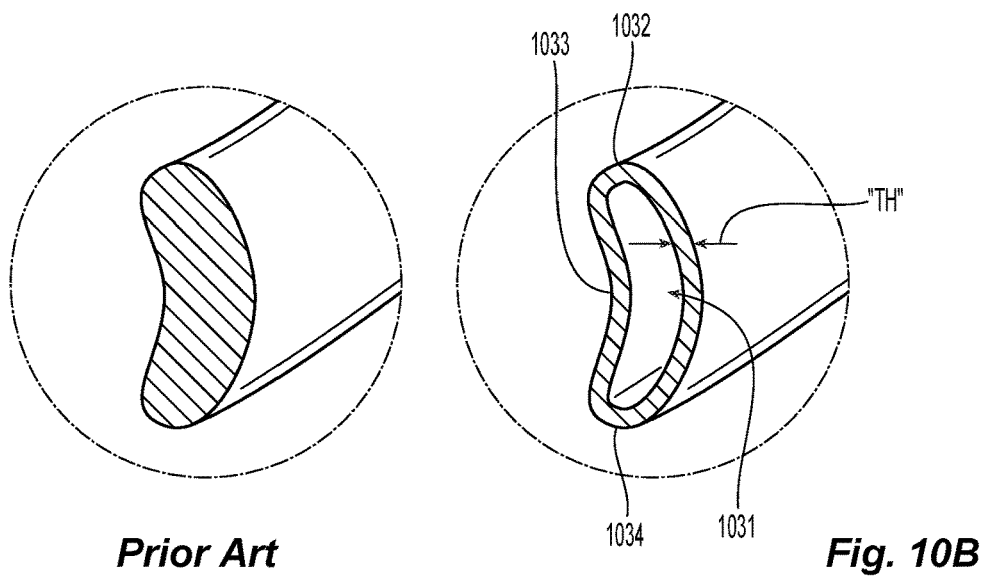
FIG. 10C is a perspective view of the bag brim of FIG. 10A shown being compressed by a forceps.
Figure 10C:
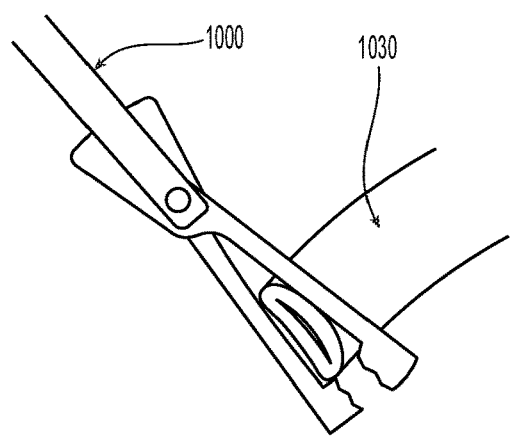

Unlike the aforedescribed bag brims, bag brim 1030 is hollow and defines an interior cavity 1031 defined therein. Cavity 1031 allows the bag brim 1030 to compress or collapse on itself facilitating grasping and handling of the bag brim 1030 by a forceps or some other grasping instrument (FIG. 10C). The bag brim 1030 may be made from any material that allows for compression thereof. A compressible gel may be infused within the cavity to promote reliable and consistent compression and expansion of the bag brim 1030 as needed.

The thickness "TH" of the bag brim 1030 walls range from about 0.035 inches to about 0.055 inches. Depending upon the particular material used for the bag brim 1030, a different thickness "TH" may be preferable to promote a balance between compressibility and furling rigidity.

If the surgeon desires to bring the specimen "T" closer to the proximal end 314 of the bag 312, the surgeon furls the bag 312 around the bag brim 1030. The D-shape of the bag brim 1030 facilitates furling the bag 312 and the brim 1030 over on itself which, in turn, allows the surgeon to position the tissue specimen "T" at a desired depth "L" within the surgical cavity depending upon a particular purpose (See FIG. 5B). The bag brim 1030 may include a high friction surface to facilitate gripping the bag 312 when furling.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval bag assembly, comprising: a tissue specimen bag having an open proximal end and a closed distal end, the proximal end including a cuff defined therein and extending therearound; and a flexible bag brim disposed within the cuff, the flexible bag brim transitionable between a first, collapsed configuration and a second, expanded configuration, the flexible bag brim including a D-Shaped cross section having a flat side and an arcuate side, the flexible bag brim configured to facilitate both furling the tissue specimen bag onto itself around the bag brim when the bag brim is disposed in the second, expanded configuration and securing the tissue specimen bag in a desired furled configuration, the flexible bag brim defining a cavity therein configured to facilitate compression thereof and to facilitate handling of the bag brim by a surgical instrument.

2. The tissue specimen retrieval bag assembly according to claim 1, wherein the tissue specimen bag is made from at least one of nylon or polyurethane.

3. The tissue specimen retrieval bag assembly according to claim 1, wherein an outer peripheral surface of the bag brim includes a high friction material to facilitate gripping the tissue specimen bag when furling.

4. The tissue specimen retrieval bag assembly according to claim 1, wherein the cavity is filled with a compressible liquid gel.

5. The tissue specimen retrieval bag assembly according to claim 1, wherein a thickness of the walls of the bag brim is in the range of about 0.035 inches to about 0.055 inches.

6. The tissue specimen retrieval bag assembly according to claim 1, wherein the thickness of the walls of the bag brim is dependent on the material of the bag brim.

* * * * *